Nov. 16, 1943. A. B. GRAF Plant Pat. 606
ROSE PLANT
Filed June 21, 1943
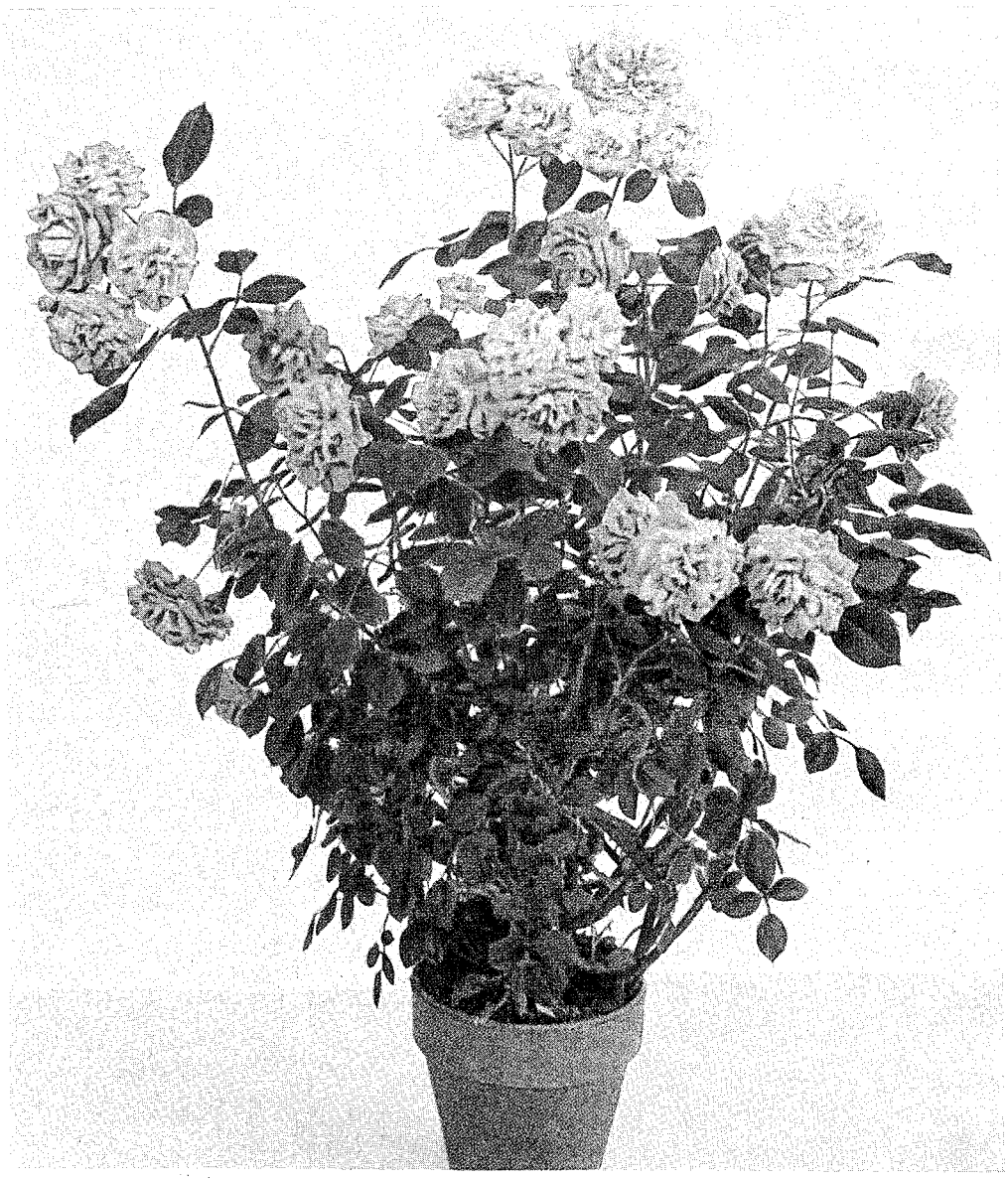
INVENTOR
Alfred B. Graf
By Orville M. Kile
Plant Pat. Agt.

Patented Nov. 16, 1943

Plant Pat. 606

UNITED STATES PATENT OFFICE

606

ROSE PLANT

Alfred B. Graf, Rutherford, N. J., assignor to
Julius Roehrs Company, Rutherford, N. J.

Application June 21, 1943, Serial No. 491,704

1 Claim. (Cl. 47—61)

My present discovery relates to a new and distinct variety of large-flowered climbing rose plant, originating as a sport on a Paul's Scarlet Climber which was among a number of plants being forced in the greenhouse.

The outstanding difference between this new rose variety and its parent is the complete doubleness of its flowers—the new flower having a petalage of from 80 to 100 compared with 20 to 26 petals which is the average for Paul's Scarlet Climber. Also outstanding as a characteristic of the new flower is its excellent lasting quality. Leaf petioles of the new variety are reddish, in contrast to the green of Paul's Scarlet Climber, and the leaves are slightly more serrated than those of the parent plant. The color of the flower is practically the same as that of its parent although possibly a shade darker. However, the new flower tends to fade much more slowly and to hold its petals for a longer time.

The accompanying illustration making up a part of this specification, shows a potted plant of this new rose variety as forced in the greenhouse and is in approximately true colors.

In the following detailed description of the flower and plant of this new rose variety, color terminology is in accordance with that of Ridgway's Color Standards and Nomenclature except where no plate number is given.

*The plant*

*Blooming habit.*—Plant is not remontant; produces a great abundance of bloom in a season.

*Growth habit.*—Climbing; vigorous.

*Canes.*—Heavy; medium green, tinged with brown at the base.

*Stems.*—Rigid; medium to heavy; approximately Biscay Green (Pl. XVII); moderate number of thorns present.

*Thorns.*—Sharp; medium in size; downward-pointing; Brick Red (Plate XIII).

*Foliage.*—Abundant; compound, with 3 to 5 leaflets.

Leaflets:

*Size.*—Terminal leaflet 2¼ inches to 3¼ inches long and 1½ inches to 2 inches wide.

*Shape.*—Almost a true oval, with the addition of an acuminate apex.

*Serrations.*—Sharp; rather deep.

*Color.*—Approximately Elm Green (Pl. XVII) on upper surface. Under surface slightly greyed.

*Stipules.*—Narrow, medium to long, clinging except for sharp points.

*Petioles.*—Red-tinged; short.

*Rachis.*—Medium to heavy; long, with considerable space between leaflets; upper side grooved and tinged with Hay's Russet (Pl. XIV); under side green with a few small prickles.

*Leaf texture.*—Substantial; leathery.

*The flower*

*Borne.*—Abundantly; in clusters.

*Fragrance.*—Moderate amount.

Bud:

*Size.*—Before calyx breaks, ¼ inch long. When calyx breaks, but before unfurling, ⅝ inch long.

*Form.*—Before calyx breaks, almost round becoming pointed as calyx opens and bud expands.

*Color.*—Bright tone of Rose Red (Pl. XII).

*Calyx.*—Approximately same color as stems. Sepals reflex early; long, extending beyond unopened bud.

Blossom:

*Size.*—When fully open, measures 2½ to 3 inches across.

*Petalage.*—Very double, from 80 to 100 petals.

*Form.*—Tightly cupped and flat-topped. When fully opened the petals are rolled at the edges so that they appear somewhat pointed. Reproductive organs are seldom visible.

*Color.*—Almost uniform in color tone. Between Rose Red (Pl. XII) and Spectrum Red (Pl. XII). Color fades very little but older blossoms lighten slightly toward Tyrian Rose (Pl. XII).

Petals:

*Substance.*—Medium.

*Aspect.*—Velvety on upper surface; dull on under surface.

*Size.*—Outer petals approximately 1¼ inches across in each dimension.

*Shape.*—Outer petals practically round; deeply cupped. Outer and intermediate petals usually have a notch at the tip; otherwise the margin is whole. Inner petals irregular and small.

Reproductive organs:

*Pistils.*—Many; bunched. *Styles* very short. *Stigmas* small and light green.

*Stamens.*—Surround bunched pistils. *Filaments* pink-tinged and longer than pistils. *Anthers* light brown.

Having thus disclosed my discovery, I claim:

The new and useful variety of climbing rose plant substantially as herein shown and described, having many of the characteristics of its parent, Paul's Scarlet Climber, but characterized particularly as to novelty by its fully double flower; its reddish leaf petioles; the clinging nature of its flower petals; and the tendency of its brilliant crimson-scarlet flowers to fade slowly.

ALFRED B. GRAF.